(12) United States Patent
Noda

(10) Patent No.: US 10,407,367 B2
(45) Date of Patent: Sep. 10, 2019

(54) SEPARATION METHOD AND SEPARATION APPARATUS

(71) Applicant: NGK INSULATORS, LTD., Nagoya (JP)

(72) Inventor: Kenichi Noda, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 15/463,224

(22) Filed: Mar. 20, 2017

(65) Prior Publication Data

US 2017/0190640 A1    Jul. 6, 2017

Related U.S. Application Data

(63) Continuation of application No. PCT/JP2015/074824, filed on Sep. 1, 2015.

(30) Foreign Application Priority Data

Sep. 29, 2014 (JP) .................................. 2014-198356

(51) Int. Cl.
| | |
|---|---|
| *B01D 71/56* | (2006.01) |
| *C07C 7/144* | (2006.01) |
| *B01D 53/04* | (2006.01) |
| *B01D 53/14* | (2006.01) |
| *C07C 7/12* | (2006.01) |
| *C07C 11/04* | (2006.01) |
| *B01D 53/22* | (2006.01) |
| *B01D 71/02* | (2006.01) |
| *B01D 63/06* | (2006.01) |
| *B01D 69/14* | (2006.01) |
| *B01D 71/00* | (2006.01) |
| *C07C 7/11* | (2006.01) |
| *C07C 7/167* | (2006.01) |
| *C10G 25/00* | (2006.01) |
| *C10G 31/09* | (2006.01) |
| *C10G 31/11* | (2006.01) |
| *C10G 45/32* | (2006.01) |

(Continued)

(52) U.S. Cl.
CPC .............. *C07C 7/144* (2013.01); *B01D 53/04* (2013.01); *B01D 53/14* (2013.01); *B01D 53/228* (2013.01); *B01D 63/066* (2013.01); *B01D 69/14* (2013.01); *B01D 71/00* (2013.01); *B01D 71/022* (2013.01); *B01D 71/028* (2013.01); *C07C 7/11* (2013.01); *C07C 7/12* (2013.01); *C07C 7/167* (2013.01); *C07C 11/04* (2013.01); *C10G 21/00* (2013.01); *C10G 25/00* (2013.01); *C10G 31/09* (2013.01); *C10G 31/11* (2013.01); *C10G 45/32* (2013.01); *C10G 53/02* (2013.01); *C10G 53/08* (2013.01); *C10G 67/02* (2013.01); *B01D 71/027* (2013.01); *B01D 71/56* (2013.01); *B01D 2252/10* (2013.01); *B01D 2252/20405* (2013.01); *B01D 2252/20468* (2013.01); *B01D 2252/20484* (2013.01); *B01D 2252/20489* (2013.01); *B01D 2253/102* (2013.01); *B01D 2253/104* (2013.01); *B01D 2253/108* (2013.01); *B01D 2257/304* (2013.01); *B01D 2257/7022* (2013.01); *B01D 2311/04* (2013.01)

(58) Field of Classification Search
CPC ...... B01D 2252/10; B01D 2252/20405; B01D 2252/20468; B01D 2252/20484; B01D 2252/20489; B01D 2253/102; B01D 2253/104; B01D 2253/108; B01D 53/04; B01D 53/14; B01D 53/228; B01D 71/022; B01D 71/028
See application file for complete search history.

(56) References Cited

U.S. PATENT DOCUMENTS

| | | |
|---|---|---|
| 5,352,272 A | 10/1994 | Moll et al. |
| 6,080,905 A | 6/2000 | Kaminski et al. |

(Continued)

FOREIGN PATENT DOCUMENTS

| | | |
|---|---|---|
| JP | 08-500054 A1 | 1/1996 |
| JP | H11-236574 A | 8/1999 |

(Continued)

OTHER PUBLICATIONS

Vladimiros Nikolakis, et al., "Growth of a Faujasite-type Zeolite Membrane and its Application in the Separation of Saturated/Unsaturated Hydrocarbon Mixtures," *Journal of Membrane Science*, vol. 184, 2001, pp. 209-219.

(Continued)

*Primary Examiner* — Sharon Pregler
(74) *Attorney, Agent, or Firm* — Burr & Brown, PLLC

(57) ABSTRACT

A separation apparatus 10 includes a pretreatment section 20 that subjects a target fluid containing an olefin compound to at least one or more of a treatment for reducing an acetylene-based compound, a treatment for reducing a sulfur compound, and a treatment for reducing a fine particle component. In the pretreatment section 20, one or more treatments selected from a hydrotreating and an adsorption treatment with an adsorbent may be performed as the treatment for reducing the acetylene-based compound, one or more treatments selected from a washing and absorption treatment, an adsorption treatment with an adsorbent, and a hydrodesulfurization treatment may be performed as the treatment for reducing the sulfur compound, and one or more treatments selected from a liquid absorption treatment, a collection treatment, or a filtration treatment with a filter may be performed as the treatment for reducing the fine particle component.

8 Claims, 5 Drawing Sheets

(51) Int. Cl.
  *C10G 53/02*  (2006.01)
  *C10G 53/08*  (2006.01)
  *C10G 67/02*  (2006.01)
  *C10G 21/00*  (2006.01)

(56) References Cited

U.S. PATENT DOCUMENTS

| | | | |
|---|---|---|---|
| 6,124,517 | A * | 9/2000 | Kaminsky .............. B01J 20/02 585/809 |
| 6,156,950 | A | 12/2000 | Ragil et al. |
| 2006/0047176 | A1 | 3/2006 | Gartside et al. |
| 2007/0012189 | A1 | 1/2007 | Kang et al. |
| 2009/0270665 | A1 | 10/2009 | Magalhaes Mendes et al. |
| 2011/0072965 | A1 | 3/2011 | Lie et al. |
| 2014/0135559 | A1 | 5/2014 | Sawamura et al. |
| 2014/0378721 | A1 | 12/2014 | Kuwana et al. |
| 2015/0141729 | A1 | 5/2015 | Noda |

FOREIGN PATENT DOCUMENTS

| | | |
|---|---|---|
| JP | 2001-514696 A | 9/2001 |
| JP | 2007-021473 A1 | 2/2007 |
| JP | 2009-029676 A | 2/2009 |
| JP | 2009-506035 A | 2/2009 |
| JP | 2011-527935 A1 | 11/2011 |
| JP | 2014-113584 A1 | 6/2014 |
| KR | 10-0499972 B1 | 7/2005 |
| WO | 2013/114667 A1 | 8/2013 |
| WO | 2014/034910 A1 | 3/2014 |

OTHER PUBLICATIONS

Masahiko Matsukata, et al., "Possibility of Propane/Propylene Separation with Silver Cation-Exchanged Y-type Zeolite Membrane," *SCEJ* (*The Society of Chemical Engineers of Japan*), 78th Annual Meeting Q109, Mar. 17-19, 2013 (with English translation).
International Search Report and Written Opinion (Application No. PCT/JP2015/074824) dated Nov. 10, 2015.
English translation of International Preliminary Report on Patentability (Chapter I) (Application No. PCT/JP2015/074824) dated Apr. 13, 2017, 7 pages.
Japanese Office Action (and translation provided by foreign counsel) from a corresponding Japanese patent application (JP 2016-551668) dated Jul. 2, 2019, 8 pages.

* cited by examiner

SEPARATION METHOD AND SEPARATION APPARATUS

BACKGROUND OF THE INVENTION

1. Field of the Invention

The present invention relates to a separation method and a separation apparatus.

2. Description of the Related Art

Hitherto, a method for separating and recovering olefin from a mixture of paraffin and olefin with a separation membrane including a porous substrate and a zeolite layer arranged on a surface of the substrate and/or in a surface layer portion of the substrate has been reported as a separation method (for example, see PTL 1 and NPLs 1 and 2). PTL 1 states that in the case where a Si/Al ratio in a zeolite layer is $1.3 \leq Si/Al \leq 3.5$ and where the separation factor α of the zeolite layer for a water-isopropanol mixture containing 15% to 30% water by weight is within a predetermined range, a separation membrane is highly selectively permeable to olefin and has good durability. NPL 1 states that propylene/propane or ethylene/methane separation can be performed with an FAU-type zeolite membrane. NPL 2 reports a method for separating one of olefin and paraffin from an olefin-paraffin mixture with a AgY-type zeolite membrane formed by ion exchange of a NaY-type zeolite membrane.

CITATION LIST

Patent Literature

PTL 1: Japanese Unexamined Patent Application Publication No. 2014-113584

Non Patent Literature

NPL 1: Journal of Membrane Science 184(2001)209-219.
NPL 2: Masahiko Matsukata and two other people, "Possibility of propane/propylene separation with silver cation-exchanged Y-type zeolite membrane", Mar. 17 to 19, 2013, SCEJ (The Society of Chemical Engineers Japan) 78th Annual Meeting Q109.

SUMMARY OF THE INVENTION

In each of the separation methods described in PTL 1 and NPL 1, however, an olefin compound is not sufficiently separated. In the separation method described in NPL 2, in the case of separating a component with a separation membrane, if a gas to be treated contains a specific component, for example, the selectivity of separation treatment and the amount of the gas subjected to separation treatment per unit time are disadvantageously reduced to reduce the efficiency of the separation treatment with the passage of separation time. Thus, the separation of an olefin compound with a separation membrane has been required to be more stably performed.

The present invention has been accomplished in light of the foregoing problems. It is a main object of the present invention to provide a separation method and a separation apparatus for more stably separating an olefin compound with a separation membrane.

The inventors have conducted intensive studies to achieve the foregoing main object and have found that the separation of an olefin compound is more stably performed by reducing a specific substance in a target fluid to be treated prior to separation treatment with a Ag-containing separation membrane. This finding has led to the completion of the present invention.

A separation method and a separation apparatus of the present invention include:

a pretreatment step of subjecting a target fluid containing an olefin compound to at least one or more of a treatment for reducing an acetylene-based compound, a treatment for reducing a sulfur compound, and a treatment for reducing a fine particle component; and a separation step of separating the olefin compound from the target fluid that has been subjected to the pretreatment with a Ag-containing separation membrane.

A separation apparatus of the present invention includes:

a pretreatment section that subjects a target fluid containing an olefin compound to at least one or more of a treatment for reducing an acetylene-based compound, a treatment for reducing a sulfur compound, and a treatment for reducing a fine particle component; and a separation section that separates the olefin compound from the target fluid that has been subjected to the pretreatment with a Ag-containing separation membrane.

The separation of the olefin compound is more stably performed by the separation method and with the separation apparatus of the present invention. The reason for this is presumably that, for example, the bonding of a Ag component in the separation membrane to the acetylene-based compound and the sulfur compound is further inhibited by reducing these compounds in the pretreatment step. Another reason for this is presumably that the clogging of the separation membrane with a fine particle component is further inhibited by reducing the fine particle component in the pretreatment step.

DETAILED DESCRIPTION OF THE INVENTION (Separation Apparatus)

Figure 1:
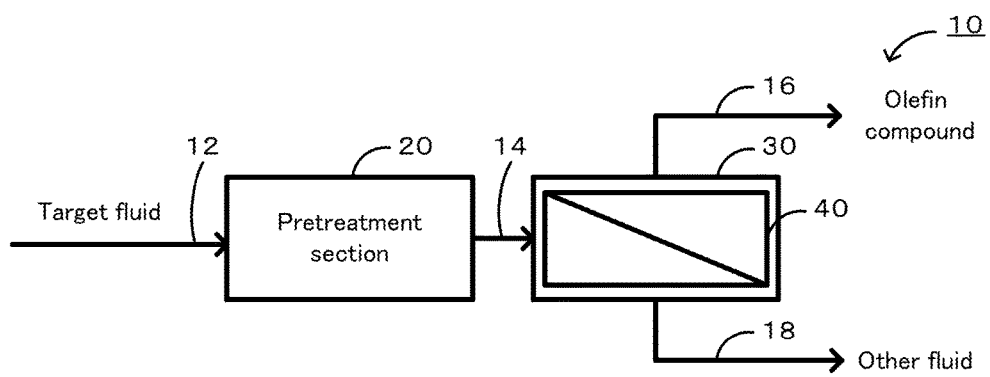
FIG. 1 is a schematic explanatory drawing of a structure of a separation apparatus 10.
Figure 2:
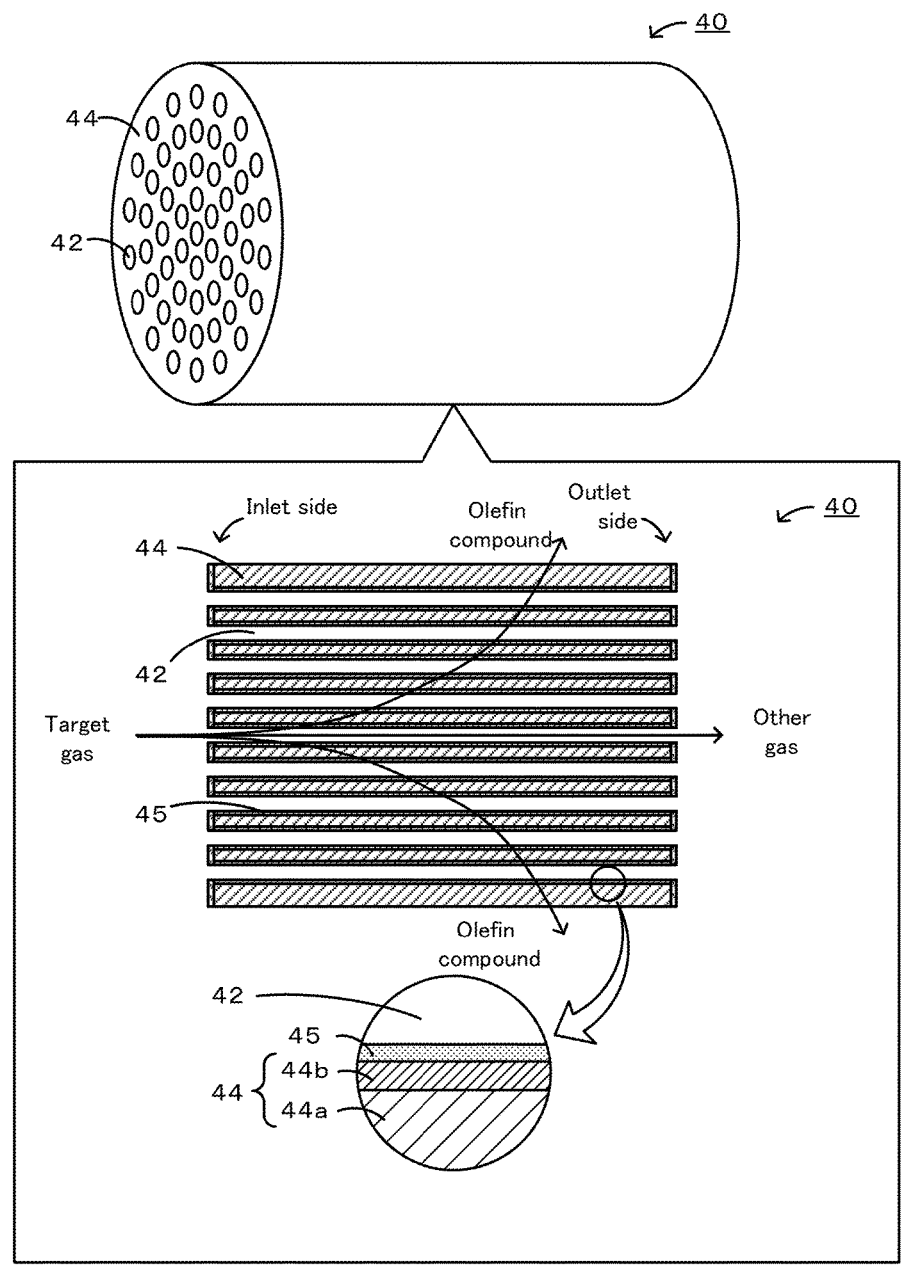
FIG. 2 is a schematic explanatory drawing of a structure of a membrane filter 40.
Figure 3:
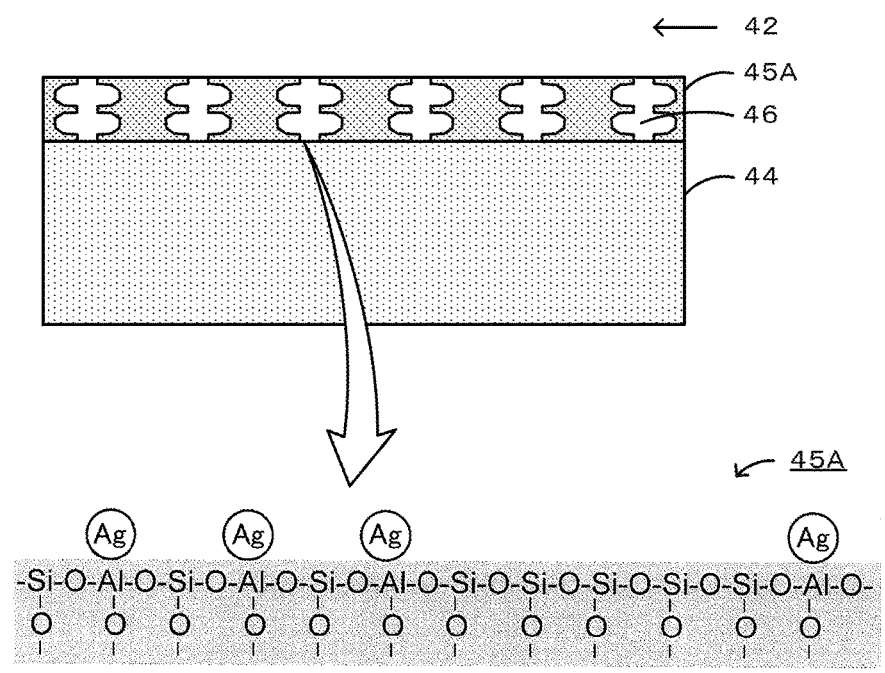
FIG. 3 is an explanatory drawing illustrating an example of a zeolite membrane 45A.
Figure 4:
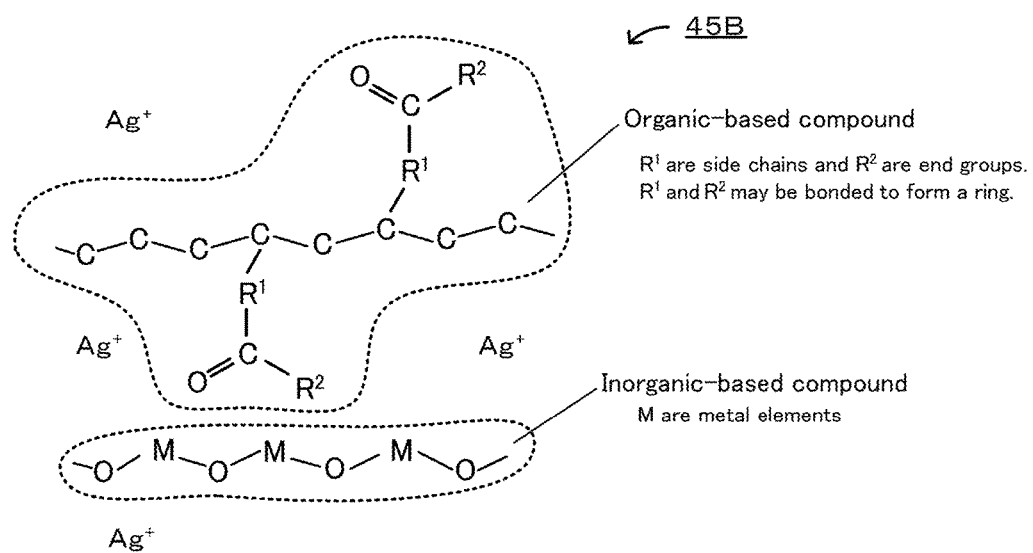
FIG. 4 is an explanatory drawing illustrating an example of an organic-inorganic hybrid membrane 45B.
Figure 5:
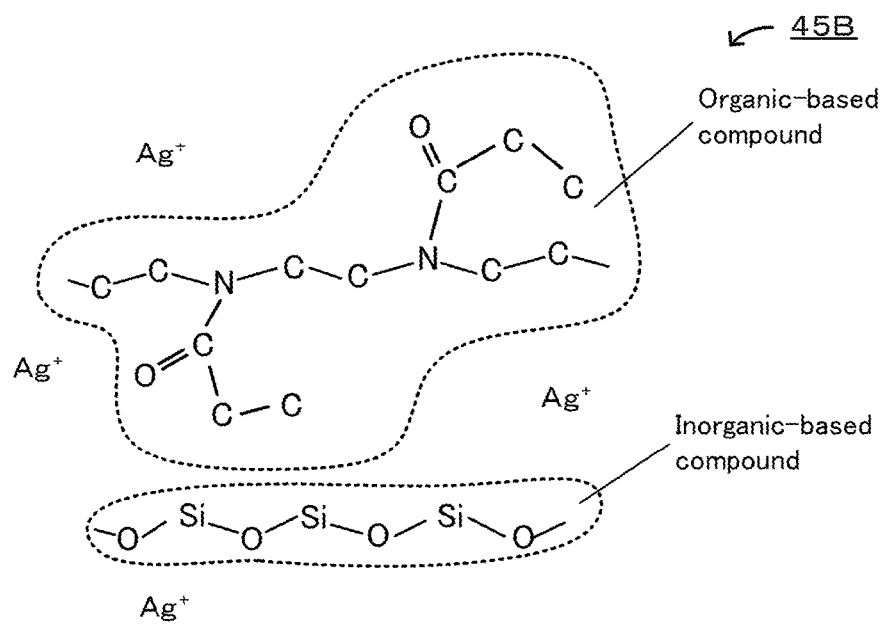
FIG. 5 is an explanatory drawing illustrating a specific example of the organic-inorganic hybrid membrane 45B.

A separation apparatus and a separation method according to an embodiment of the present invention will be described with reference to the drawings. FIG. 1 is a schematic explanatory drawing of a structure of the separation apparatus 10. FIG. 2 is a schematic explanatory drawing of a structure of the membrane filter 40. FIG. 3 is an explanatory drawing illustrating a zeolite membrane 45A that is an example of separation membranes 45. FIG. 4 is an explanatory drawing illustrating an organic-inorganic hybrid membrane 45B that is an example of the separation membranes 45. FIG. 5 is an explanatory drawing illustrating a specific example of the organic-inorganic hybrid membrane 45B. The separation apparatus 10 is an apparatus for separating an olefin compound from a target fluid containing an olefin compound.

A target fluid to be treated may be an olefin compound-containing fluid (mainly a gas). The target fluid to be treated may contain a paraffin compound or an inorganic gas in addition to the olefin compound. The target fluid to be treated may also contain an acetylene-based compound, a sulfur compound, a fine particle component, or other components. Examples of the olefin compound include ethylene, propylene, and derivatives thereof. Examples of the paraffin include methane, ethane, propane, and derivatives thereof. Examples of the inorganic gas include nitrogen, oxygen, carbon dioxide, hydrogen, carbon monoxide, and noble gases. The fluid includes a gas, a liquid, and so forth. The concentration of the olefin compound in the target fluid to be treated may be 40% or more by volume, 50% or more by volume, 60% or more by volume, or 70% or more by volume. The concentration of the paraffin compound and the inorganic gas in the target fluid to be treated may be 60% or less by volume, 50% or less by volume, 40% or less by volume, or 30% or less by volume.

The separation apparatus 10 includes a pretreatment section 20 and a separation section 30 as illustrated in FIG. 1. The separation apparatus 10 further include a supply flow path 12 that supplies the target fluid to be treated to the pretreatment section 20, a flow path 14 connected between the pretreatment section 20 and the separation section 30, a flow path 16 through which the olefin compound that has permeated the membrane filter 40 of the separation section 30 passes, and a flow path 18 through which a fluid (a fluid containing substances except the olefin compound) that has not permeated the membrane filter 40 of the separation section 30 passes.

The pretreatment section 20 serves as a device that subjects the target fluid containing the olefin compound to at least one or more of a treatment for reducing an acetylene-based compound, a treatment for reducing a sulfur compound, a treatment for reducing a fine particle component. The pretreatment section 20 may perform one or more treatments selected from a hydrotreating and an adsorption treatment with an adsorbent as the treatment for reducing the acetylene-based compound. The pretreatment section 20 may perform one or more treatments selected from a washing and absorption treatment, an adsorption treatment with an adsorbent, and a hydrodesulfurization treatment as the treatment for reducing the sulfur compound. The pretreatment section 20 may perform one or more treatments selected from a liquid absorption treatment, a collection treatment, and a filtration treatment with a filter as the treatment for reducing the fine particle component. The pretreatment section 20 may perform the treatments for reducing the acetylene-based compound and the fine particle component, the treatments for reducing the sulfur compound and the fine particle component, or the treatments for reducing the acetylene-based compound and the sulfur compound. For example, when the adsorption treatment is performed, the pretreatment section 20 includes an adsorption portion including an adsorbent. When the hydrotreating or the hydrodesulfurization treatment is performed, the pretreatment section 20 includes a reaction portion including a catalyst. When the washing and absorption treatment or the liquid absorption treatment is performed, an absorption portion including a solvent or an absorbing liquid is provided. The pretreatment section 20 includes two or more of the adsorption portion, the reaction portion, and the absorption portion when multiple treatments are performed. Details of these pretreatments will be described in "Separation method".

The separation section 30 serves as a device that performs a treatment for separating the olefin compound from the target fluid that has been subjected to the pretreatment in the pretreatment section 20. In the separation section 30, the membrane filter 40 may include a one or two or more filters. The separation section 30 includes the membrane filter 40 including the separation membranes 45 (see FIG. 2) that contains Ag and that is selectively permeable to the olefin compound. As illustrated in FIG. 2, the membrane filter 40 includes a porous substrate 44 that defines cells 42 serving as flow paths of the target fluid; and the separation membranes 45 that are arranged on inner surfaces of the porous substrate 44 and that have a separation function for the target fluid. As described above, the separation membranes 45 are arranged on the surfaces of the porous substrate 44; hence, even if the separation membranes 45 are thin membranes, the form thereof is maintained by supporting the thin membranes by the porous substrate 44, thus preventing breakage or the like. In the membrane filter 40, the olefin compound in the target fluid that enters the cells 42 from an inlet side permeates the separation membranes 45 owing to the action of Ag ions and then permeates the porous substrate 44 to exit from a side face of the membrane filter 40. A fluid (mainly the paraffin compound or the inorganic gas) that cannot permeate the separation membranes 45 passes through the flow paths of the cells 42 and exits from the outlet side of the cells 42. The porous substrate 44 may have a monolithic structure including the cells 42 or a tubular structure including a single cell. The external form thereof is not particularly limited and may be a cylindrical form, an elliptic cylindrical form, a quadrangular prismatic form, a hexagonal prismatic form, or the like. The porous base 44 may have a tubular form with a polygonal cross section.

As the porous base 44, a ceramic, a metal, a resin, or the like may be used. In particular, a porous ceramic material is preferred. As aggregate particles of the porous ceramic material, alumina, titania, mullite, potsherds, cordierite, and so forth may be used. In view of availability, stability of a green body, and corrosion resistance, alumina is particularly preferred. The porous substrate 44 may contain an inorganic binder in addition to the porous material. As the inorganic binder, one or more of titania, mullite, sinterable alumina, silica, glass frits, clay minerals, and sinterable cordierite may be used. The porous substrate 44 may have a porosity of 25% or more by volume and 50% or less by volume. The porous substrate 44 may have an average pore size of 0.05 μm or more and 25 μm or less. The porous material contained in the porous substrate 44 may have an average particle diameter of 0.1 μm or more and 100 μm or less. The porous substrate 44 may have a multilayer structure (two-or-more-layer structure) in which a fine grained portion 44b having a small pore size is arranged on a surface of a coarse grained portion 44a having a large pore size. The coarse grained portion 44a may have a pore size of, for example, about 0.1 μm to about several hundred micrometers. The fine grained portion 44b may have a smaller pore size than the coarse grained portion 44a and, for example, may have a pore size of about 0.001 to about 1 μm. In this case, the porous substrate 44 has reduced permeation resistance. The "average particle diameter" indicates the arithmetic mean of maximum diameters of 30 target particles measured by the observation of a cross-sectional microstructure with a scanning electron microscope (SEM). The "average pore size" indicates a value measured with Perm Porometer or Nano Perm Porometer selected depending on pore size.

Each of the separation membranes 45 selectively separates the olefin compound from the target fluid by permeation and may be, for example, one or more of the zeolite membrane 45A containing Ag (see FIG. 3) and the organic-inorganic hybrid membrane 45B containing Ag (see FIGS. 4 and 5). In view of the long-term stability of the membrane material against olefin, a Ag-containing zeolite membrane is preferred. A Ag component contained in the separation membranes 45 may be metallic Ag or a Ag ion. The Ag component is preferably the Ag ions because the function of the Ag component can be provided in a smaller amount. When the Ag component is metallic Ag, its particle diameter D50 is preferably, for example, 1 nm or more and 10 nm or less. When the Ag component is the Ag ion, the Ag ion may be contained in the form of a salt of the Ag ion and an anion, for example, $PF_6-$, $BF_4-$, $ClO_4-$, or $NO_3-$, that is, for example, $AgPF_6$, $AgBF_4$, $AgClO_4$, or $AgNO_3$. While the separation of the olefin compound from the paraffin compound with the separation membranes 45 will be described below, the present invention is not limited to the following separation examples.

The zeolite membrane 45A is arranged on the inner surface of each of the cells 42 of the porous substrate 44. The zeolite membrane 45A has a crystal structure selected from FAU (Y-type, X-type), LTA (A-type), LTL (L-type), MFI, MEL, MOR, MWW, FER, BEA, and so forth. The zeolite membrane 45A has the function of selectively permeate olefin. Micropores 46 in the zeolite membrane 45A preferably have a maximum internal diameter of 0.4 nm or more and 0.8 nm or less. A maximum internal diameter of 0.4 nm or more results in a high olefin permeance, which is preferred. A maximum internal diameter of 0.8 nm or less results in high olefin separation performance, which is preferred. The zeolite membrane 45A preferably has a thickness of 10 μm or less and more preferably 3 μm or less in view of the olefin permeance. In FIG. 3, three-dimensional atomic arrangement is illustrated in two dimensions, but actually each of Si, which is a tetravalent element, and Al, which is a trivalent element, forms four covalent bonds. The zeolite membrane 45A at least contains Si, Al, and Ag and may further contain at least one of alkali metals and alkaline-earth metals. Examples of alkali metals include Li, Na, K, Rb, Cs, and Fr. Examples of alkaline-earth metals include Mg, Ca, Sr, Ba, and Ra. The zeolite membrane 45A has a structure in which $SiO_4$ tetrahedrons and $AlO_4$ tetrahedrons share oxygen vertices with each other and are three-dimensionally connected together. To balance the charge misfit due to the presence of Al, which has a lower valence than Si, the micropores contains Ag in an ionic state. The Ag ions are more likely to form a complex with the olefin compound than the paraffin compound. Thus, the olefin compound can migrate in the micropores by repeating the formation and dissociation of the complex of the olefin compound and the Ag ion. The presence of the olefin compound prevents the paraffin compound from entering the micropores. Thereby, the zeolite membrane 45A provides olefin/paraffin separation performance. The separation performance, which indicates an olefin/paraffin separation function, of the membrane filter 40 including the zeolite membranes 45A is preferably 2 or more, more preferably 5 or more, still more preferably 10 or more, and particularly preferably 50 or more. The separation performance is determined as described below. An olefin/paraffin (1:1 (on a mol % basis)) gas mixture is supplied to the membrane filter 40 at a temperature of 23° C. and a pressure of 0.7 MPa. The amount of a gas that has permeated the membrane filter is measured with a mass flow meter under conditions where a pressure on the permeation side of the membrane filter 40 is 0.1 MPa, and the composition of the gas is measured by gas chromatography. The permeance rate of each of olefin and paraffin is calculated from the amount permeated and the gas composition. (Olefin permeance)/(paraffin permeance) is defined as the separation performance. The permeance indicates the amount of a gas that permeates the membrane filter 40 per unit pressure difference, unit membrane area, and unit time and is given in units of $[mol/(m^2 \cdot s \cdot Pa)]$. Higher separation performance (olefin separation performance) results in a higher gas separation function. Ethylene serving as the olefin and ethane serving as the paraffin are used for the measurement of the separation performance.

The organic-inorganic hybrid membrane 45B is arranged on each of the inner surfaces of the cells 42 of the porous substrate 44. The organic-inorganic hybrid membrane 45B contains a carbonyl group-containing organic-based compound, a metal component-containing inorganic-based compound, and a Ag component as illustrated in FIG. 4. The inorganic-based compound may have, for example, a metal matrix structure. The metal matrix structure may be, for example, a chain structure or three-dimensional structure of a metal and oxygen. The metal matrix structure may have a functional group bonded to the metal. The functional group may be bonded to the main chain or a side chain of the metal matrix structure. Examples of the side chain include hydrocarbon groups that may have a substituent having about 1 to about 10 carbon atoms. The side chain may contain one or more of N, O, S, and P. The inorganic-based compound may be a compound containing O and one or more elements selected from Si, Ti, Al, and Zr. In compounds containing these metals, structures having high mechanical strength are easily formed because of bonding with oxygen. In compounds containing these metals, chain structures or three-dimensional structures are easily formed, which is preferred. The inorganic-based compound may be a hydrolysate of a metal alkoxide. The metal alkoxide is preferred because it is easily hydrolyzed and polymerized. In the case where the metal is Si, examples of the metal alkoxide include tetramethoxysilane, tetraethoxysilane, methyltriethoxysilane, ethyltrimethoxysilane, and phenyltrimethoxysilane. In the case where the metal is Ti, an example of the metal alkoxide is tetraisopropoxytitanium.

The organic-based compound contained in the organic-inorganic hybrid membrane 45B may have a carbon structure in which carbon atoms are bonded together and a carbonyl group bonded to the carbon structure. The carbon structure may be a chain structure or three-dimensional structure. The carbon structure may contain one or more of N, O, S, and P in a main chain or a side chain. The carbonyl group may be bonded to the main chain or the side chain of the carbon structure. An example of such a carbon structure is a polymer. In the case where the polymer has a carbonyl group in its main chain, examples of the polymer include polyesters (such as polyethylene terephthalate and polyarylate), polycarbonates, polyamides, and polyurethanes. In the case where the polymer has a carbonyl group in its side chain, examples of the polymer include polyvinylpyrrolidone (PVP), poly(2-ethyl-2-oxazoline) (POZ), polyvinyl acetate (PVAc), and polymethyl methacrylate (PMMA). In the organic-inorganic hybrid material of the present invention, the organic-based compound and the inorganic-based compound are uniformly mixed together; hence, the Ag component is easily dispersed. As a result, the Ag component is less likely to aggregate even if a large amount of Ag component is contained.

In the organic-inorganic hybrid membrane 45B, the ratio of the number of metal atoms of the inorganic-based compound to the number of carbon atoms of the organic-based compound, i.e., M/C, may be 0.04 or more and 1.60 or less. When M/C is 0.04 or more, the swelling of the organic-based compound, in particular, under high pressure is seemingly inhibited by the inorganic-based compound combined with the organic-based compound, thereby inhibiting the degradation of the separation performance. When M/C is 1.60 or less, the structure does not contain an excessively large amount of the inorganic-based compound; hence, a hydrocarbon gas seemingly dissolves easily in the organic-inorganic hybrid material, so that the gas is satisfactorily transmitted. The ratio M/C is preferably 0.08 or more and more preferably 0.22 or more, and preferably 1.50 or less and more preferably 1.32 or less. M/C is determined as described below. Ten points of a surface of the organic-inorganic hybrid material are subjected to X-ray photoelectron spectroscopy (XPS). The ratio of the number of metal atoms of the inorganic-based compound to the number of carbon atoms of the organic-based compound at each of the measurement points is determined, and the average value of the resulting ratios is calculated and used as M/C.

In the organic-inorganic hybrid membrane 45B, the ratio of the number of silver atom of the Ag component to the number of carbon atoms of the organic-based compound, i.e., Ag/C, may be 0.07 or more and 0.55 or less. When Ag/C is 0.07 or more, for example, affinity with the olefin compound is seemingly improved to enhance the separation performance. When Ag/C is 0.55 or less, defects due to the aggregation of an excessive amount of the Ag component are seemingly less likely to be formed, thereby inhibiting the degradation of the separation performance. Ag/C is preferably 0.10 or more and more preferably 0.20 or more, and preferably 0.50 or less and more preferably 0.40 or less. As with M/C, Ag/C may be determined by XPS. In the organic-inorganic hybrid membrane 45B, the separation performance, which indicates an olefin/paraffin separation function, is preferably 10 or more, more preferably 30 or more, and still more preferably 50 or more. For example, the organic-inorganic hybrid membrane 45B may include the inorganic-based compound having a metal matrix structure including metal M and oxygen, the organic-based compound containing carbonyl groups, and silver ions, as illustrated in FIG. 4. In FIG. 4, each of the carbonyl groups is bonded to side chain $R^1$ of the organic-based compound and has end group $R^2$. A specific example of the organic-inorganic hybrid material is a material including an inorganic-based compound having a Si matrix structure, an amide group-containing polymer serving as an organic-based compound, and Ag ions (see FIG. 5).

The domain size of the organic-inorganic hybrid material of the organic-inorganic hybrid membrane 45B is preferably 20 nm or less and more preferably 10 nm or less. The "domain size" used here indicates the size of the structural unit of the organic-inorganic hybrid material. When an inorganic material and an organic material are formed into a hybrid material in a state in which the domain size is small, for example, the hybrid material seemingly has good mechanical strength. Furthermore, the Ag component seems to be uniformly dispersed. The domain size is measured as described below. Photographing is performed in freely-selected 10 fields of view on a cross section of the organic-inorganic hybrid material with a scanning electron microscope (SEM). In each of the resulting images, regions having different compositions are separated by energy dispersive X-ray spectroscopy (EDS). Specifically, regions each including an inorganic skeleton containing a metal, for example, Si, Ti, Al, or Zr, in the inorganic-based compound (hereinafter, also referred to as "inorganic regions") and regions each composed of an organic material (hereinafter, also referred to as "organic regions") are separated from each other. Here, in the case where each of the inorganic regions is close to white (or black) and where each of the organic regions is close to black (or white) in the resulting images, the inorganic regions and the organic regions may be separated from each other on the basis of the contrast. The cross section of the organic-inorganic hybrid material is photographed with the SEM at a magnification of ×2000 to ×5000. The domain size is defined as the maximum lengths (longitudinal diameters) of the inorganic regions and the organic regions in the images, and this domain size is measured. In the case where in two or more fields of view of the 10 fields of view in SEM observation, a domain having a size of 0.1 µm or more accounts for 5% or more of the area of one image, the domain size is rated as 0.1 µm or more. In the case where the SEM observation indicates that there is no domain having a size of 0.1 µm or more, a cross section of the organic-inorganic hybrid material is photographed with a transmission electron microscope (TEM) at a magnification of ×200,000. Regions having different compositions are separated from each other by the EDS. Specifically, the regions are separated into the inorganic regions and the organic regions. As with the case of using the SEM, the domain size is measured. The size of all domains in the 10 fields of view is measured by the foregoing method and the average value of the size is used as the domain size of the organic-inorganic hybrid material. A smaller domain size indicates that the organic-based compound and the inorganic-based compound are more uniformly mixed together.

A method for producing the organic-inorganic hybrid membrane 45B may include a combination step of preparing an organic-inorganic hybrid material, in which a carbonyl group-containing substance is used as a raw material for the organic-based compound, a metal component-containing substance is used as a raw material for the inorganic-based compound in such a manner that the ratio of the number of metal atoms to the number of carbon atoms of the raw material for the organic-based compound is 0.04 or more and 1.60 or less, and a raw material for the Ag component is used in such a manner that the ratio of the number of silver atoms to the number of carbon atoms of the raw material for the organic-based compound is 0.07 or more and 0.55 or less.

(Separation Method)

A separation method of the present invention includes a pretreatment step of subjecting a target fluid containing an olefin compound to a treatment for reducing a predetermined component; and a separation step of separating the olefin compound from the target fluid that has been subjected to pretreatment with a Ag-containing separation membrane. The separation method may be performed with the separation apparatus 10.

(Pretreatment Step)

In this step, the target fluid is subjected to at least one or more of a treatment for reducing an acetylene-based compound, a treatment for reducing a sulfur compound, and a treatment for reducing a fine particle component.

As the treatment for reducing the acetylene-based compound, one or more treatments selected from a hydrotreating and an adsorption treatment with an adsorbent are used. The target fluid prior to separation treatment preferably has an acetylene-based compound content of 100 ppm or less, more preferably 50 ppm or less, still more preferably 10 ppm or less, and particularly preferably 1 ppm or less. At a content of 100 ppm or less, the separation membrane is further maintained in performance when used continuously. The acetylene-based compound is a compound having a carbon-carbon triple bond (alkynyl group) and includes a compound having a terminal alkyne group and a compound having an internal alkyne group. Examples thereof include acetylene, methylacetylene, 1-butyne, and 2-pentine.

An example of the hydrotreating of the acetylene-based compound is selective hydrotreating over a catalyst. In the selective hydrotreating, the carbon-carbon triple bond of the acetylene-based compound is preferably converted into a carbon-carbon double bond by hydrogenation. In this case, the olefin compound is increased, which is preferred. An example of the catalyst is a catalyst in which a metal component containing one or more of Pd, Cs, Mg, and Zn is supported on a carrier. Of these, Pd is preferred as the metal component. The carrier is not limited as long as it supports the metal component in a highly dispersed state. Examples of the carrier include alumina, silica, silica-alumina, zirconia, zeolite, mullite, cordierite, and clay. Examples of zeolite include zeolites having crystal structures of FAU (Y-type, X-type), LTA (A-type), LTL (L-type), MFI, MEL, MOR, MWW, FER, BEA, and so forth. The carrier is preferably composed of alumina. The amount of the metal component supported may be appropriately selected and is preferably, for example, 0.001% or more by mass and 2% or less by mass with respect to the whole catalyst including the metal component and the carrier. The catalyst preferably contains 0.005% or more by mass and 1% or less by mass Pd with respect to the whole catalyst. The selective hydrotreating is performed by adding hydrogen gas to the target fluid at a predetermined hydrogenation temperature. The amount of hydrogen gas added is preferably, for example, 1 or more times by mole and 5 or less times by mole with respect to the acetylene-based compound in the target fluid. The hydrogenation temperature may be, for example, normal temperature or higher and 200° C. or lower. The selective hydrotreating may be performed in the range of normal pressure or more and 30 atm or less.

In the adsorption treatment of the acetylene-based compound with the adsorbent, an example of the adsorbent is an adsorbent in which one or more metal components selected from Cr, Fe, Co, Ni, Ru, Pd, and Pt are dispersed on a carrier. Of these, Pd is preferred as the metal component. The adsorbent may also contain a metal component, for example, Li, Na, K, Zn, Mo, Sn, W, or Ir. The carrier may be selected from the foregoing materials, activated carbon, and so forth. Of these, alumina is preferred. The adsorbent may be a mixture of activated alumina and zeolite. Activated alumina is a material produced by transforming aluminum hydroxide into porous aluminum oxide having low crystallinity. The activated alumina preferably has an average pore size, which is determined by nitrogen adsorption, of 1 nm or more and 100 nm or less. The zeolite may be selected from, for example, the foregoing materials and is preferably FAU. The adsorption temperature may be in the range of 0° C. to 100° C. In the adsorption treatment, the contact time may be in the range of 0.1 hours to 100 hours, and the contact pressure may be in the range of 0.2 MPa to 5 MPa.

As the treatment for reducing the sulfur compound, one or more treatments selected from an adsorption treatment with an adsorbent, a washing and absorption treatment, and a hydrodesulfurization treatment are used. The target fluid prior to separation treatment preferably has a sulfur compound content of 0.1 ppm or less, more preferably 0.05 ppm or less, and still more preferably 0.02 ppm or less. At a content of 0.1 ppm or less, the separation membrane is further maintained in performance when used continuously. Examples of the sulfur compound include hydrogen sulfide, sulfur oxide, carbonyl sulfide, and organic sulfur compounds, such as sulfur-containing hydrocarbon compounds and sulfur-containing heterocyclic compounds. Examples of organic sulfur compounds include thiophene compounds. Thiophene compounds are compounds including a thiophene structure and include thiophene, benzothiophene, and derivatives thereof.

In the adsorption treatment of the sulfur compound with the adsorbent, an example of the adsorbent is an adsorbent in which one or more metal components selected from Ni, Cu, and Pd are supported on a carrier is used as the adsorbent. The carrier may be selected from the foregoing materials. Of these, alumina is preferred. The amount of the metal components supported is preferably 2% or more by mass and 20% or less by mass. Furthermore, examples of the adsorbent include activated carbon, zeolite, silica gel, alumina, CoMo adsorbents, activated coke, adsorbents impregnated with metals, and mixtures thereof. The adsorption temperature may be in the range of, for example, 0° C. to 100° C. In this adsorbent treatment, the target fluid may be introduced at a linear velocity of 5 cm/h to 25 cm/h. The contact pressure may be in the range of 0.1 MPa to 1 MPa.

In the washing and absorption treatment of the sulfur compound, the gas of the target fluid is subjected to washing and absorption with a solvent to remove the sulfur compound. Examples of the solvent include alkaline solvents, such as an aqueous sodium solution and an aqueous potassium solution, alcohols, m-methylpyrrolidone, monomethanolamine, diethanolamine, triethanolamine, hot potassium carbonate, and sodium hypochlorite. In the washing and absorption treatment, a treatment is performed in which the target gas is passed through the solvent to trap the sulfur compound in the solvent.

In the hydrodesulfurization treatment of the sulfur compound, a treatment is performed in which the target fluid containing hydrogen gas is brought into contact with a hydrodesulfurization catalyst to remove the sulfur compound. The hydrodesulfurization catalyst may be a catalyst in which any of Fe, Ni, and Co and any of Mo and W are contained as catalytic components and in which the catalytic components are supported on a carrier. The catalytic components are preferably Co and Mo. The carrier may be selected from the foregoing materials. Of these, alumina, silica, silica-alumina, or the like is preferred. The amount of the catalytic components supported is preferably 0.5% or more by mass and 4% or less by mass with respect to the mass of the whole catalyst. The reaction temperature of the hydrodesulfurization treatment is preferably 100° C. or higher and 400° C. or lower and more preferably 200° C. or higher and 300° C. or lower. In the hydrodesulfurization treatment, hydrogen sulfide formed by reaction over the hydrodesulfurization catalyst may be removed by the washing and absorption treatment.

As the treatment for reducing the fine particle component, one or more treatments selected from a liquid absorption treatment, a collection treatment, and a filtration treatment with a filter are used. The target fluid prior to separation treatment preferably has a fine particle component content of 10 mg/m$^3$ or less, more preferably 1 mg/m$^3$ or less, and still more preferably 0.1 mg/m$^3$ or less. At a content of 10 mg/m$^3$ or less, the separation membrane is further maintained in performance when used continuously. The fine particle component refers to particles having a particle diameter of, for example, 10 μm or less and preferably 1 μm or less. The composition is not particularly limited and may contain C, Si, Al, or the like. The particle diameter of the fine particle component is determined by observation and measurement with, a scanning electron microscope (SEM).

In the liquid absorption treatment of the fine particle component, for example, the gas of the target fluid is passed through an absorption liquid, and the fine particle component is absorbed in the absorption liquid and thereby removed. Examples of the absorption liquid include water; and organic solvents, such as alcohols and acetone. When water is used as the absorption liquid, the addition of a surfactant or the like is preferred. The absorption liquid may be in the form of bubbles formed by blowing a gas, for example, nitrogen or air, into the absorption liquid. In this case, the fine particle component is easily removed by the bubbles.

In the collection treatment of the fine particle component, for example, a treatment may be performed in which the fine particle component that has been electrically charged is attached to an electrode. The applied voltage to the electrode may be appropriately set, depending on the content and the particle diameter of the fine particle component. The fine particle component attached to the electrode may be removed by washing.

In the filtration treatment of the fine particle component with the filter, examples of the filter that may be used include polymer filters, ceramic filters, and metal filters. The filter may be selected, depending on the size of the fine particle component to be filtered. For example, filters having a pore size of 0.1 μm to 1 μm may be used. Examples of materials of the polymer filters include fluororesins, polyimide resins, polysulfone resins, cellulose, and polycarbonate resins. Examples of materials of the ceramic filters include alumina, silica, mullite, and cordierite. An example of materials of the metal filters is stainless steel. The fine particle component filtered by the filter is recovered by shaking off the fine particle component from the filter or a backwashing treatment.

The pretreatment step may be performed by performing the treatment for reducing the acetylene-based compound and the treatment for reducing the fine particle component; the treatment for reducing the sulfur compound and the treatment for reducing the fine particle component; or the treatment for reducing the acetylene-based compound and the treatment for reducing the sulfur compound. In this case, two or more treatments are preferably performed using a common operation as much as possible. For example, in the case where the sulfur compound is removed by the washing and absorption treatment and where the fine particle component is removed by the liquid absorption treatment, the sulfur compound and the fine particle component can be reduced in one operation by the use of a solution having functions of the solvent and the absorption liquid. In the case where the acetylene-based compound is removed by the adsorption treatment with the adsorbent and where the sulfur compound is removed by the adsorption treatment with the adsorbent, both substances can be reduced in one operation by the use of an adsorbent that adsorbs both substances or a mixture of two types of adsorbents. In the case where the acetylene-based compound is reduced by the selective hydrotreating and where the sulfur compound is reduced by the hydrodesulfurization treatment, the addition of hydrogen to the target gas to be treated is a common operation; hence, the treatments can be performed more easily. In the case where two or more treatments are performed, the treatments that are not inhibited by each other are preferably selected. For example, an adsorbent supporting a metal component may hydrogenate olefin in the presence of hydrogen. In the pretreatment step, the three treatments for reducing the acetylene-based compound, the sulfur compound, and the fine particle component may be performed.

According to the separation method and the separation apparatus of the present invention described above, the acetylene-based compound and the sulfur compound are reduced in the pretreatment step, thus further inhibiting the bonding of these compounds to the Ag component in the separation membrane. Moreover, the fine particle component is reduced in the pretreatment step, thus further inhibiting the clogging of the separation membrane with the fine particle component. Therefore, the separation of the olefin compound is performed more stably in the present invention.

The present invention is not limited to the above-described embodiment, and can be carried out by various modes as long as they belong to the technical scope of the invention.

For example, while the hydrotreating and the adsorption treatment with the adsorbent are described as the treatment for reducing the acetylene-based compound in the foregoing embodiments, any method for reducing the acetylene-based compound may be employed without particular limitation. While the washing and absorption treatment, the adsorption treatment with the adsorbent, and the hydrodesulfurization treatment are described as the treatment for reducing the sulfur compound, any method for reducing the sulfur compound may be employed without particular limitation. While the liquid absorption treatment, the collection treatment, and the filtration treatment with the filter are described as the treatment for reducing the fine particle component, any method for reducing the fine particle component may be employed without particular limitation. Furthermore, one impurity (for example, the acetylene-based compound) may be subjected to a plurality of reduction treatments (for example, the hydrotreating and the adsorption treatment).

In the foregoing embodiments, while one or more of the Ag-containing zeolite membrane and the organic-inorganic hybrid membrane containing Ag are used as the separation membrane, any Ag-containing separation membrane that separates the olefin compound may be used without particular limitation.

EXAMPLES

Specific examples of the present invention will be described below as experimental examples. It is needless to mention that the scope of the present invention is not limited to the following examples and the present invention may be carried out in other various embodiments without departing from the technical scope of the invention.

Experimental Example 1

A precursor sol serving as a precursor of an organic-inorganic hybrid material was synthesized. First, 0.7 g of poly(2-ethyl-2-oxazoline) serving as a polymer and 5.7 g of ethanol serving as a solvent were mixed together to prepare a polymer solution. To the polymer solution, 0.3 g of tetraethoxysilane serving as a raw material of an inorganic-based compound was added. The resulting solution was stirred. To the solution, 0.09 g of water (at a molar ratio of 4 with respect to tetraethoxysilane) and 0.004 g of nitric acid (at a molar ratio of 0.03 with respect to tetraethoxysilane) serving as a catalyst were added. The resulting mixture was stirred for 16 hours to allow the hydrolysis and polymerization of tetraethoxysilane to proceed. To this solution, 1.4 g of $AgBF_4$ was added, and the resulting mixture was stirred to give a precursor sol. In this precursor sol, the ratio of the number of Si atoms of tetraethoxysilane to the number of C atoms of poly(2-ethyl-2-oxazoline), i.e., (Si/C), was 0.04. The ratio of the number of Ag atoms of AgBF$_4$ to the number of C atoms of poly(2-ethyl-2-oxazoline), i.e., (Ag/C), was 0.20. The precursor sol was applied on a porous alumina substrate having a diameter of 10 mm, a length of 10 cm, and a surface pore size of 0.1 µm by dip coating and dried overnight in a N$_2$ atmosphere at room temperature, thereby producing a membrane filter of Experimental example 1. One end portion of the membrane filter was sealed, and the other end portion was connected to a glass tube.

Experimental Example 2

Colloidal silica serving as a silicon source, sodium aluminate serving as an aluminum source, sodium hydroxide serving as an alkali source, tetrapropylammonium hydroxide serving as a structure-directing agent, and water serving as a solvent were stirred to prepare a raw-material solution. The raw-material solution was poured into a stainless-steel pressure-resistant vessel (equipped with an inner cylinder composed of a fluororesin) having an inner capacity of 100 ml. Then a porous alumina substrate having a diameter of 10 mm, a length of 10 cm, and a surface pore size of 0.1 µm was immersed therein and subjected to heat treatment (hydrothermal synthesis) at 120° C. for 25 hours to provide a separation membrane structure. The separation membrane structure produced by the hydrothermal synthesis was washed with water, dried at 80° C., and heated (400° C. for 4 hours) with an electric furnace in air to remove the structure-directing agent by combustion. The resulting separation membrane structure was immersed in an aqueous solution of 0.1 mol/L silver nitrate for 24 hours to perform Ag-ion exchange. The separation membrane structure that has been subjected to Ag-ion exchange was washed with water and dried at 80° C. to provide a membrane filter of Experimental example 2. A surface of the separation membrane structure was subjected to XRD measurement to identify the crystalline phase (type of zeolite). The crystalline phase of Experimental example 2 indicated MFI-type zeolite. The average pore size of the zeolite was calculated from the crystalline phase and found to be 0.54 nm. One end portion of the membrane filter was sealed, and the other end portion was connected to a glass tube.

(Evaluation of Gas Separation)

The gas separation with the membrane filters of Experimental examples 1 and 2 was evaluated. Regarding the evaluation of gas separation, gases in which an impurity component was added to an ethylene/ethane (1:1 (on a mol % by basis)) gas mixture was used. In the case where acetylene was used as the impurity component, the gases had acetylene concentrations of 100 ppm and 500 ppm and were used for Experimental examples 1A, 1B, 2A, and 2B. In the case where hydrogen sulfide in place of acetylene was used as the impurity component, the gases had hydrogen sulfide concentrations of 0.1 ppm and 0.5 ppm and were used for Experimental examples 1C, 1D, 2C, and 2D. In the case where a fine particle component was used as the impurity component, the gases had fine particle component concentrations of 10 mg/m$^3$ and 50 mg/m$^3$ and were used for Experimental examples 1E, 1F, 2E, and 2F. With respect to the evaluation of gas separation, the foregoing gas mixtures were continuously supplied to the membrane filters for 24 hours under measurement conditions of a temperature of 23° C., a pressure on the supply side of 0.7 MPa, and a pressure on the permeation side of 0.1 MPa. The amounts of the gases that had permeated the membrane filters were measured with a mass flow meter. The compositions of the gases were measured by gas chromatography. From these results, the permeance rate of each of ethylene and ethane was calculated. From the calculation results, ethylene permeance/ethane permeance was defined as the separation performance. (Separation performance after a lapse of 24 hours)/(separation performance after a lapse of 1 hour)×100(%) was defined as a separation performance maintenance ratio.

(Results and Discussion)

Table 1 summarizes the structures of the membrane filters, the impurities and their concentrations in the target gas to be treated, and the separation performance maintenance ratios in Experimental examples 1A to 1F and 2A to 2F. A separation performance maintenance ratio of 80% or more was rated as "A", and a separation performance maintenance ratio less than 80% was rated as "B". As listed in Table 1, it was found that the separation performance maintenance ratios of both the membrane filters of Experimental examples 1 and 2 are reduced when acetylene serving as an acetylene-based compound is present in the target gas to be treated in a concentration of 500 ppm or more. Similarly, it was found that the separation performance maintenance ratios of both the membrane filters of Experimental examples 1 and 2 are reduced when hydrogen sulfide serving as a sulfur compound is present in the target gas to be treated in a concentration of 0.5 ppm or more. It was also found that the separation performance maintenance ratios of both the membrane filters of Experimental examples 1 and 2 are reduced when the fine particle component is present in the target gas to be treated in a concentration of 50 mg/m$^3$ or more. In contrast, it was found that in the cases where the concentration of acetylene is 100 ppm or less, the concentration of hydrogen sulfide is 0.1 ppm or less, and where the concentration of the fine particle component is 10 mg/m$^3$ or less, acetylene, hydrogen sulfide, and the fine particle component serving as the impurity components, a reduction in separation performance maintenance ratio is inhibited in all the cases, and the separation of the olefin compound with each of the separation membranes is more stably performed. The reason for this is presumably that while the presence of the acetylene-based compound and the sulfur compound serving as the impurity components in the target fluid to be treated seemingly causes an adverse effect, such as bonding to Ag of the separation membranes, the membrane filters further inhibit the adverse effect.

TABLE 1

| | Membrane filter | Impurity | Content | Separation performance maintenance ratio |
|---|---|---|---|---|
| Experimental example 1A | Organic-inorganic hybrid membrane | Acetylene | 100 ppm | A |
| Experimental example 1B | Organic-inorganic hybrid membrane | Acetylene | 500 ppm | B |
| Experimental example 1C | Organic-inorganic hybrid membrane | Hydrogen sulfide | 0.1 ppm | A |
| Experimental example 1D | Organic-inorganic hybrid membrane | Hydrogen sulfide | 0.5 ppm | B |

TABLE 1-continued

|  | Membrane filter | Impurity | Content | Separation performance maintenance ratio |
|---|---|---|---|---|
| Experimental example 1E | Organic-inorganic hybrid membrane | Fine particle component | 10 mg/m$^3$ | A |
| Experimental example 1F | Organic-inorganic hybrid membrane | Fine particle component | 50 mg/m$^3$ | B |
| Experimental example 2A | Zeolite membrane | Acetylene | 100 ppm | A |
| Experimental example 2B | Zeolite membrane | Acetylene | 500 ppm | B |
| Experimental example 2C | Zeolite membrane | Hydrogen sulfide | 0.1 ppm | A |
| Experimental example 2D | Zeolite membrane | Hydrogen sulfide | 0.5 ppm | B |
| Experimental example 2E | Zeolite membrane | Fine particle component | 10 mg/m$^3$ | A |
| Experimental example 2F | Zeolite membrane | Fine particle component | 50 mg/m$^3$ | B |

The present application claims priority from Japanese Patent Application No. 2014-198356 filed on Sep. 29, 2014, the entire contents of which are incorporated herein by reference.

What is claimed is:

1. A separation method, comprising:
a pretreatment step of subjecting a target fluid containing an olefin compound to at least one or more of a treatment for reducing an acetylene-based compound, a treatment for reducing a sulfur compound, and a treatment for reducing a fine particle component; and
a separation step of directing the target fluid into an inlet of a separation structure comprising a porous substrate carrying an Ag-containing separation membrane, wherein the olefin compound from the target fluid that has been subjected to the pretreatment step passes through the separation membrane and the remaining portion of the target fluid is exhausted from an outlet of the separation structure without passing through the separation membrane.

2. The separation method according to claim 1, wherein in the pretreatment step, one or more treatments selected from a hydrotreating and an adsorption treatment with an adsorbent are performed as the treatment for reducing the acetylene-based compound.

3. The separation method according to claim 1, wherein in the pretreatment step, one or more treatments selected from a washing and absorption treatment, an adsorption treatment with an adsorbent, and a hydrodesulfurization treatment are performed as the treatment for reducing the sulfur compound.

4. The separation method according to claim 1, wherein in the pretreatment step, one or more treatments selected from a liquid absorption treatment, a collection treatment, and a filtration treatment with a filter are performed as the treatment for reducing the fine particle component.

5. The separation method according to claim 1, wherein in the pretreatment step, the treatment for reducing the acetylene-based compound and the treatment for reducing the fine particle component are performed, the treatment for reducing the sulfur compound and the treatment for reducing the fine particle component are performed, or the treatment for reducing the acetylene-based compound and the treatment for reducing the sulfur compound are performed.

6. The separation method according to claim 1, wherein in the separation step, one or more of a Ag-containing zeolite membrane and a Ag-containing organic-inorganic hybrid membrane are used as the separation membrane.

7. The separation method according to claim 1, wherein in the separation step, one or more of Ag-containing zeolite membranes having LTA-type, LTL-type, MFI-type, MEL-type, MOR-type, MWW-type, FER-type, and BEA-type crystal structures are used as the separation membrane.

8. The separation method according to claim 1, wherein in the separation step, a Ag-containing zeolite membrane having an MFI-type crystal structure is used as the separation membrane.

* * * * *